(12) United States Patent
Deshmukh

(10) Patent No.: US 9,284,244 B2
(45) Date of Patent: Mar. 15, 2016

(54) CARBOXYLIC ACID SALT REMOVAL DURING HYDRATE INHIBITOR RECOVERY

(71) Applicant: Fjords Processing AS, Lysaker (NO)

(72) Inventor: Salim Deshmukh, Oslo (NO)

(73) Assignee: FJORDS PROCESSING AS, Lysaker (NO)

( * ) Notice: Subject to any disclaimer, the term of this patent is extended or adjusted under 35 U.S.C. 154(b) by 0 days.

(21) Appl. No.: 14/399,339

(22) PCT Filed: May 6, 2013

(86) PCT No.: PCT/IB2013/053617
§ 371 (c)(1),
(2) Date: Nov. 6, 2014

(87) PCT Pub. No.: WO2013/168077
PCT Pub. Date: Nov. 14, 2013

(65) Prior Publication Data
US 2015/0119609 A1    Apr. 30, 2015

(30) Foreign Application Priority Data
May 11, 2012   (NO) .................................... 20120547

(51) Int. Cl.
| | |
|---|---|
| C07C 29/88 | (2006.01) |
| C07C 29/86 | (2006.01) |
| C07C 41/38 | (2006.01) |
| C07C 41/44 | (2006.01) |
| B01D 61/00 | (2006.01) |
| B01D 3/34 | (2006.01) |
| B01D 9/00 | (2006.01) |
| C10L 3/10 | (2006.01) |

(52) U.S. Cl.
CPC . *C07C 29/88* (2013.01); *B01D 3/34* (2013.01); *B01D 9/0054* (2013.01); *B01D 61/00* (2013.01); *C07C 29/86* (2013.01); *C07C 41/38* (2013.01); *C07C 41/44* (2013.01); *B01D 2311/2642* (2013.01); *C09K 2208/22* (2013.01); *C10L 3/107* (2013.01); *C10L 2290/12* (2013.01)

(58) Field of Classification Search
CPC ........ C07C 29/86; C07C 29/88; C07C 41/38; C07C 41/44
See application file for complete search history.

(56) References Cited

U.S. PATENT DOCUMENTS

| | | | |
|---|---|---|---|
| 4,026,681 A | | 5/1977 | Roskelley |
| 4,105,701 A | * | 8/1978 | Larkin .......................... 570/211 |
| 6,340,373 B1 | | 1/2002 | Billington |
| 6,425,942 B1 | | 7/2002 | Forster |
| 2005/0072663 A1 | | 4/2005 | Laborie et al. |
| 2010/0191023 A1 | | 7/2010 | Chen |
| 2013/0118989 A1 | | 5/2013 | Caires Fernandez |

FOREIGN PATENT DOCUMENTS

| | | | |
|---|---|---|---|
| EP | 0 971 776 | | 1/2000 |
| GB | 2 467 169 | | 7/2010 |
| WO | 2005/092470 | | 10/2005 |
| WO | 2007/073204 | | 6/2007 |
| WO | 2009/017971 | | 2/2009 |
| WO | WO 2011028131 A1 | * | 3/2011 ............. C07C 29/76 |

OTHER PUBLICATIONS

Database CAPLUS in STN, Acc. No. 1975:478574, Yamamoto et al., JP 50035105 A (Apr. 3, 1975) (abstract).*
Norwegian Search Report issued Nov. 14, 2012 in Norwegian Application No. 20120547.
International Search Report issued Sep. 12, 2013 in International (PCT) Application No. PCT/IB/2013/053617 along with the Written Opinion.

* cited by examiner

*Primary Examiner* — Brian J Davis
(74) *Attorney, Agent, or Firm* — Wenderoth, Lind & Ponack, L.L.P.

(57) ABSTRACT

A method and system for precipitation and separation of carboxylic acid salts from a hydrate inhibitor solution is disclosed. The method comprises lowering the solubility of the carboxylic acid salts to force precipitation of carboxylic acid salts and separation of the precipitated carboxylic acid salts from the hydrate inhibitor solution.

14 Claims, 10 Drawing Sheets ions of the present invention

CARBOXYLIC ACID SALT REMOVAL DURING HYDRATE INHIBITOR RECOVERY

The present invention relates to a method and system for removal of carboxylic acid salts as a part of a method or system for recovery of hydrate inhibitor (HI). Especially the present invention relates to prolonging the reuse of HI by including removal of carboxylic acid salts that would otherwise over time increase in concentration in the HI and lead to decreased quality and limit the reuse thereof.

BACKGROUND

It is well known that well streams containing a mixture of fluids such as crude oil, condensate, formation water and gas during transportation may react and form solid hydrates resulting in i.e. blocked pipelines. To avoid and or limit the formation of hydrates inhibitors are added to the well stream prior to transportation. One often applied hydrate inhibitor is mono-ethylene glycol (MEG); other applicable hydrate inhibitors include glycol compounds with other substituents, as well as kinetic hydrate inhibitors or a combination thereof. The term kinetic refers to the effect of the inhibitor lowering the reaction rate of the hydrate forming reactions.

Hydrate inhibitors such as MEG are valuable chemicals and the recycling thereof provides reduced costs. However equally important are the environmental consequences, as waste streams containing not inconsiderable amounts of MEG or similar inhibitors can not be released to the environment.

A number of different steps and methods for separating MEG for reuse are known in the art.

After a first separation of hydrocarbons the process fluid normally comprises a hydrocarbon rest, water, corrosion products, MEG and dissolved inorganic salts. Normally the amount of inorganic salts is considerable and the salts may precipitate during the MEG extraction process which again leads to increased viscosity, sludge formation or plugging. Depending on the formation the composition of the inorganic salts will vary. It is well known to remove salts from solutions by precipitation of solids by increasing the activity or concentration; however the combination of alkali and earth alkali ions, and halogen, carbonate and bicarbonate ions results in the precipitation of relatively small salt particles that are not easily separated from the solution. A further obstacle for the regeneration process is degradation of the inhibitor at high temperatures which limits the possibility to use heating to obtain separation.

Monoethylene glycol (MEG) is added to gas transport pipelines to avoid gas hydrate formation in long tie backs. Gas, MEG, $H_2O$ are separated downstream of the pipeline at the receiving facilities. MEG at these facilities contains formation water, condensed water and salts. This MEG is regenerated in a MEG reclamation plant by removing salts and water, ensuring that the MEG is reusable. Salts arriving at the MEG Regeneration system are in the form of dissociated ions and come primarily from the well's formation water, pipeline corrosion and chemical injection (pH stabiliser). Some of these salts are also from organic acids (formic, acetic, propanoic, butanoic etc.) in the formation water and gas; these are sometimes also called volatile fatty acids (VFA). Sodium and potassium salts of carboxylic acids (acetate, formate, propionate, butrate, etc.) are highly soluble in MEG under reclaimer conditions. Solubility of these salts increases with increase in temperature and hence it is not possible to precipitate the salts of carboxylic acids in the reclaimer. Since these salts are not precipitated in the reclaimer, they are not removed from the MEG system and they keep on accumulating in the reclaimer as dissolved salts. Beyond a certain accumulation they increase the viscosity of the reclaimer slurry and thereby influence the performance of the pumps and heat exchangers. At the moment there is no proven technology to precipitate/remove the salts of carboxylic acids from the MEG reclaimer.

PRIOR ART

Different technical solutions have been developed to extract inhibitor and handle the inorganic salt problem. Examples of these techniques are disclosed in U.S. Pat. No. 6,340,373 and US2005/0072663 and US2010/0191023.

US2010/0191023 disclose a reclamation process adapted to form calcium carbonate particles with increased particle size which can be removed in a filtration unit.

U.S. Pat. No. 6,340,373 discloses a method where a part of the inhibitor and a part of the water is evaporated, and the vapour phase is removed, separated and condensed forming an inhibitor stream applicable for reuse. The rest comprises mainly inhibitor and inorganic salts and is fed to a reduction and crystallization unit where a part of the salts are precipitated and removed. The particle separation can be performed in several steps. The obtained particle stream will in addition to salt particles contain a glycol rest and a water rest.

US2005/0072663 describe a process for regeneration of a glycol solution where the solution is expanded, distilled and fed to a regeneration column under vacuum to remove water and precipitate the salts, where after the salts are separated from the glycol. The separation of the salts is performed employing a centrifugal separation device. Thereby a salt stream is obtained, however this salt stream also comprises a glycol rest.

The prior art is focused on the removal of inorganic salts from the hydrate inhibitor whereas the removal of organic acid salts is not discussed.

OBJECTIVES OF THE INVENTION

The aim of the present invention is to provide a method and system for precipitating out salts of carboxylic acids in the reclaimer or outside the reclaimer in a separate system.

A further aim is to increase the lifetime of a hydrate inhibitor allowing it to be recycled for a longer time and/or an increased number of times.

A further goal is to provide a continuous system that can be connected to existing continuously running inhibitor regenerating systems. Further the invention aims at providing a method which can be performed at conditions which do not result in degradation of the hydrate inhibitor.

The present inventors have come up with solutions to reach these goals.

The present inventors have surprisingly found that the removal of carboxylic acid salts can be achieved by limiting the solubility of these salts.

According to a first aspect the present invention provides a method for precipitation and separation of carboxylic acid salts from a hydrate inhibitor fluid stream comprising lowering the solubility of the carboxylic acid salts to force precipitation of carboxylic acid salts and separation of the precipitated carboxylic acid salts by separation of the solid precipitated salts from the hydrate inhibitor solution.

In one aspect of the present invention the lowering of the solubility is performed by adding a solution of an inorganic salt comprising divalent cations. In a further aspect the divalent cations are selected from the group comprising $Ca^{2+}$, $Ba^{2+}$, $Sr^{2+}$, $Mg^{2+}$, and $Fe^{2+}$. In a special embodiment the inorganic salt is $BaCl_2$.

In another aspect of the present invention the lowering of the solubility is performed by adding at least one antisolvent to the hydrate inhibitor fluid stream. In one embodiment the antisolvent is selected from the group comprising alcohol and ketones such as methanol, ethanol, butanol, iso-propanol, acetone, butanone and pentanone, or any mixture of these. In one embodiment of the invention the at least one antisolvent is selected from methanol, ethanol, butanol, iso-propanol, acetone or a mixture thereof.

In an additional aspect of the present invention the lowering of the solubility is performed by adding a solution of inorganic salt comprising divalent cations combined with adding an antisolvent to the hydrate inhibitor fluid stream.

The term "hydrate inhibitor" as used herein refers to glycol based hydrate inhibitors such as MEG (monoethylene glycol), DEG (diethylene glycol) and TEG (triethylen glycol) as well as kinetic hydrate inhibitors known to influence the kinetics of the hydrate forming reactions or mixtures thereof. In one aspect of the present invention the hydrate inhibitor comprises at least one glycol based inhibitor. In another aspect the hydrate inhibitor is selected from MEG, DEG and TEG or a mixture thereof. Even a system initially comprising mainly MEG might later comprise DEG and or TEG due to decomposition, for example by excess heating.

In one aspect of the present invention the hydrate inhibitor is MEG.

The method according to the present invention may be employed both in connection with a full stream reclaimer and in a slipstream reclaimer. According to one aspect of the present invention the method is performed on a slip stream from a partly lean hydrate inhibitor recycle stream. The reclaimer provides a salt free or lean hydrate inhibitor stream which is mixed with the remaining partly lean hydrate inhibitor to form a lean hydrate inhibitor stream with a salt concentration low enough for use as a hydrate inhibitor in a well stream. The term partly lean hydrate inhibitor refers to a concentrated hydrate inhibitor stream from which part of the solids have been removed; the lean MEG concentration has been obtained through water removal.

In one aspect of the method according to the present invention where antisolvent is employed in connection with a slip stream reclaimer, the method comprises separation of the added antisolvent after the separation of solids, and here at least part of the heat for the evaporation and separation of the antisolvent is transferred from the remaining partly lean hydrate inhibitor stream. The heat aids the separation of the antisolvent through evaporation. Utilizing the heat from the partly lean hydrate inhibitor stream increases the energy efficiency of the method.

In a second aspect the present invention provides a hydrate inhibitor reclamation system comprising a reclaimer for evaporation of hydrate inhibitor and up-concentration and precipitation of inorganic salts comprising a rich hydrate inhibitor fluid stream inlet, a vapour outlet in fluid communication with a condenser for condensation and recovery of the hydrate inhibitor, the reclaimer further comprises a bottom fluid outlet and a return liquid inlet, wherein the bottom fluid outlet is in fluid communication with a solid separation unit comprising a return liquid outlet and a solid outlet, wherein the return liquid outlet is in fluid communication with the return liquid inlet of the reclaimer, wherein the reclaimer further comprises a divalent cation solution inlet.

In a third aspect the present invention provides a hydrate inhibitor reclamation system comprising a reclaimer for evaporation of hydrate inhibitor and up-concentration and precipitation of inorganic salts comprising a rich hydrate inhibitor fluid stream inlet, a vapour outlet in fluid communication with a condenser for condensation and recovery of the hydrate inhibitor, the reclaimer further comprises a bottom fluid outlet and a return liquid inlet wherein the bottom fluid outlet is in fluid communication with a solid separation unit comprising a return liquid outlet and a solid outlet, wherein the return liquid outlet is in fluid communication with the return liquid inlet of the reclaimer via a liquid return line, wherein the bottom fluid outlet is in fluid communication with a precipitation tank upstream the solid separation unit and the precipitation tank comprises an antisolvent inlet, wherein an antisolvent separation unit comprising an antisolvent outlet is arranged on the liquid return line downstream the solid separation unit and the antisolvent outlet is in fluid communication with the antisolvent inlet. In a system according to the third aspect the precipitation tank may further comprise a divalent cation solution inlet.

The system according to the second and third aspect may further be a slipstream system, where the system comprises a fluid stream splitter upstream the rich hydrate inhibitor fluid stream inlet. If the system further upstream comprises initial solid removal (pretreatment) and up concentration than the fluid stream through the splitter will be a partly lean hydrate inhibitor stream, and the partly rich inhibitor stream will enter the reclaimer through the rich hydrate inhibitor fluid inlet.

In the aspect with the slip stream the system may further comprise a heat exchanger arranged on the liquid return line between the solid separation unit and the antisolvent separation unit, where the heat exchanger is further in fluid communication with the fluid splitter, for transferring heat from the hydrate fluid stream not entering the reclaimer to the liquid in the liquid return line upstream the antisolvent separation unit.

In one embodiment of the present invention the hydrate inhibitor is MEG and the maximum temperature experienced by the MEG is kept below 200-220° C., preferably below 180-200° C.

The term "divalent cations" as used here refers to earth alkali cations such as $Ca^{2+}$, $Ba^{2+}$, $Sr^{2+}$, $Mg^{2+}$, other inorganic divalent ions such as $Fe^{2+}$ or mixtures thereof. In formation water and rich inhibitor fluid divalent cations are present as a variety of dissolved and/or precipitated salts. The divalent cations added in embodiments of the present invention are water soluble salts such as chlorides like $BaCl_2$. These can be applied in the form of divalent cation salt solutions in solvents such as water, alcohol or hydrate inhibitor.

The term "carboxylic acids salts" as used here refers to salts of organic acids (formic, acetic, propanoic, butanoic etc.) with Na, K, Ca, Mg, Ba, Sr, Fe etc.

Examples of the precipitated carboxylic acid salts that will form with the divalent cations include but are not limited to salts of the formula $X^{2+}(RCOO^-)_2$ where $X^2$ is the divalent cation and R is the organic rest of the carboxylic acid and R is selected from the group comprising straight or branched $C_1$-$C_{10}$-alkyl, normally $C_1$-$C_6$-alkyl.

If other carboxylic acids for instance where R is $C_2$-$C_6$-alkenyl, $C_2$-$C_6$-alkynyl are present these are likely to precipitate as carboxylic acid salts of the same form.

The partly rich hydrate inhibitor stream comprises dissolved monovalent inorganic salts such as NaCl and KCl in addition to dissolved carboxylic acid salts. If the solubility of the carboxylic acid salts is reduced to below the solubility threshold the formation of solid monovalent carboxylic acid salts takes place. Examples of the precipitated monovalent carboxylic acid salts that will form with the monovalent cations such as $Na^+$, and $K^+$ include but are not limited to salts of the formula $X^+(RCOO^-)$ where $X^+$ is the monovalent cation and R is the organic rest of the carboxylic acid and R is selected from the group comprising $C_1$-$C_{10}$-alkyl, normally $C_1$-$C_6$-alkyl. If other carboxylic acids for instance where R is $C_2$-$C_6$-alkenyl, $C_2$-$C_6$-alkynyl are present these are likely to precipitate as carboxylic acid salts of the same form.

The term antisolvent as used here preferably refers to compounds with the formula $R_1$—CO—$R_2$, or the formula $R_1$—OH or the formula HO—$R_2$—OH, where $R_1$ is selected from the group comprising straight or branched $C_1$-$C_{10}$-alkyl, $C_2$-$C_7$-alkenyl, and $R_2$ is selected from the group comprising straight or branched $C_1$-$C_8$-alkylene. Examples of applicable antisolvents include alcohols such as methanol, ethanol, isopropanol, etc. and ketones such as acetone etc.

Some prior art reclamation systems comprise a pretreatment step comprising an initial separation of inorganic salts comprising divalent cations, examples of these inorganic salts are $CaCO_3$ and $FeCO_3$. These salts have very low/no solubility, in water and hydrate inhibitor at these conditions. In slip stream systems where only a part of the hydrate inhibitor is fed to the reclaimer, the initial separation of these inorganic salts is necessary to avoid salt particles being returned to the well stream. Surprisingly, in the present invention this pretreatment can be combined with a downstream addition of a solution comprising divalent inorganic cations, where the divalent cations will result in the formation of solid carboxylic acid salts. These solid salts can be removed from the hydrate inhibitor through solid separation. According to this embodiment of the invention inorganic divalent cations are first removed according to conventional pretreatment technique then in a downstream process inorganic divalent cations are added to provide for precipitation of carboxylic acid salts.

One principle applicable in the present invention is the use of other cations for forced precipitation (e.g. as a salt of divalent cations, Ba-carboxylate, Ca-carboxylate etc.) It is known that Na and K salts of carboxylic acids are highly soluble in HI such as MEG at elevated temperatures (100 to 150° C.) under reclaimer conditions. In fact carboxylic acids are also highly soluble with other HI solutions such as MEG, DEG, TEG or mixtures thereof, and in a mixture of KHI with glycol based HI solutions, or any mixtures thereof. However, it is suggested that carboxylate salts with divalent cations (Ba, Ca, Mg, Sr) are less soluble in HI solutions such as MEG or mixtures comprising MEG at elevated temperatures under reclaimer conditions. When salts of carboxylic acids with divalent cations are less soluble under reclaimer conditions, chlorides or other soluble counter ion salts of the divalent cations can be added to the reclaimer to force precipitation of carboxylates e.g. as Ba-acetates etc. This applies to all the aforementioned divalent cations and carboxylates found in the formation water. Chlorides or other solvable salts of the divalent cations can be added as water soluble salts to the reclaimer. Once these carboxylate salts are precipitated in the reclaimer they can be removed from the reclaimer slurry together with other salts using a centrifuge or another solid/liquid separation unit. These precipitation reactions can also be achieved in separate equipment outside the reclaimer if suitable and desired. During the precipitation the temperature is preferably 0 to 130° C. and more preferably lower temperature such as 0 to 100° C., even more preferably 0 to 70° C. will be used so that maximum amounts of carboxylate salts are precipitated. The reclaimer temperature is normally 100° C. and above depending upon feed composition, if lower temperatures are desired precipitation is allowed to take place outside the reclaimer. The amount of divalent cations added to the hydrate inhibitor should preferably be adjusted to be stoichiometric or close to stoichiometric. The same principle will also apply for precipitation of carbocyclic acid salts in other HI solutions such as DEG, TEG, KHI solutions, any or mixtures thereof. An alternative principle to provide for precipitation of carboxylic acid salts is based on the use of alcohols or ketones as antisolvents.

Mono and divalent salts of carboxylic acids have lower solubility in antisolvents (such as methanol, ethanol, isopropanol, acetone etc.) than in water and MEG. This antisolvent property of the alcohols and ketones is utilised to precipitate mono and divalent salts of carboxylic acids. This can be achieved both in situ in the reclaimer or in separate equipment outside the reclaimer if suitable and desired. If performed in a separate equipment this prevents any upsets in the operation of the main reclaimer. The steps involved to precipitate out mono and divalent salts of the carboxylic acids will be as follows:

1) Antisolvent can be added into a precipitation tank to reduce the solubility of the salts. During the precipitation the temperature is preferably 0 to 130° C. and more preferably lower temperature such as 0 to 100° C., even more preferably 0 to 70° C. will be used so that maximum amounts of carboxylate salts are precipitated with minimum amount of antisolvent.
2) Upon precipitation of the mono and/or divalent salts of organic acids, solids can be removed by rotary separator (e.g. centrifuge), gravity settling or by using any another solid-liquid separation equipment but not limited to this equipment only.
3) Solid free HI-Antisolvent mixture will be heated to boil and separate antisolvent from the mixture. Separated antisolvent can be reused in step 1. Alternatively membrane separation process can be used to separate antisolvent from the solid free HI-antisolvent mixture.
4) Carboxylate salt free and antisolvent free HI will be recycled back to the reclaimer.

BRIEF DESCRIPTION OF THE DRAWINGS

The present invention will be described in further detail with reference to the enclosed figures where.

PRINCIPAL DESCRIPTION OF THE INVENTION

The present invention is directed towards a system and method for precipitation and separation of carboxylic acid salts during reclamation of hydrate inhibitor. In the different embodiments of the present invention the precipitation of these salts, which are normally soluble in the hydrate inhibitor, is obtain by changing the solubility through different processes or a combination thereof.

The optional initial pre-treatment step of hydrate inhibitor regeneration consists of removal of divalent inorganic salts. In the reclamation process solid alkali salts such as NaCl, KCl etc. are removed.

One of the commonly used hydrate inhibitors is mono-ethylene-glycol (MEG). MEG as well as other known inhibitors is sensitive to degradation and higher temperatures and therefore the temperature through out the whole process should be kept below the degradation temperature. For MEG the maximum temperature should be below 200-220° C. preferably below 180-200° C.

Figure 1:
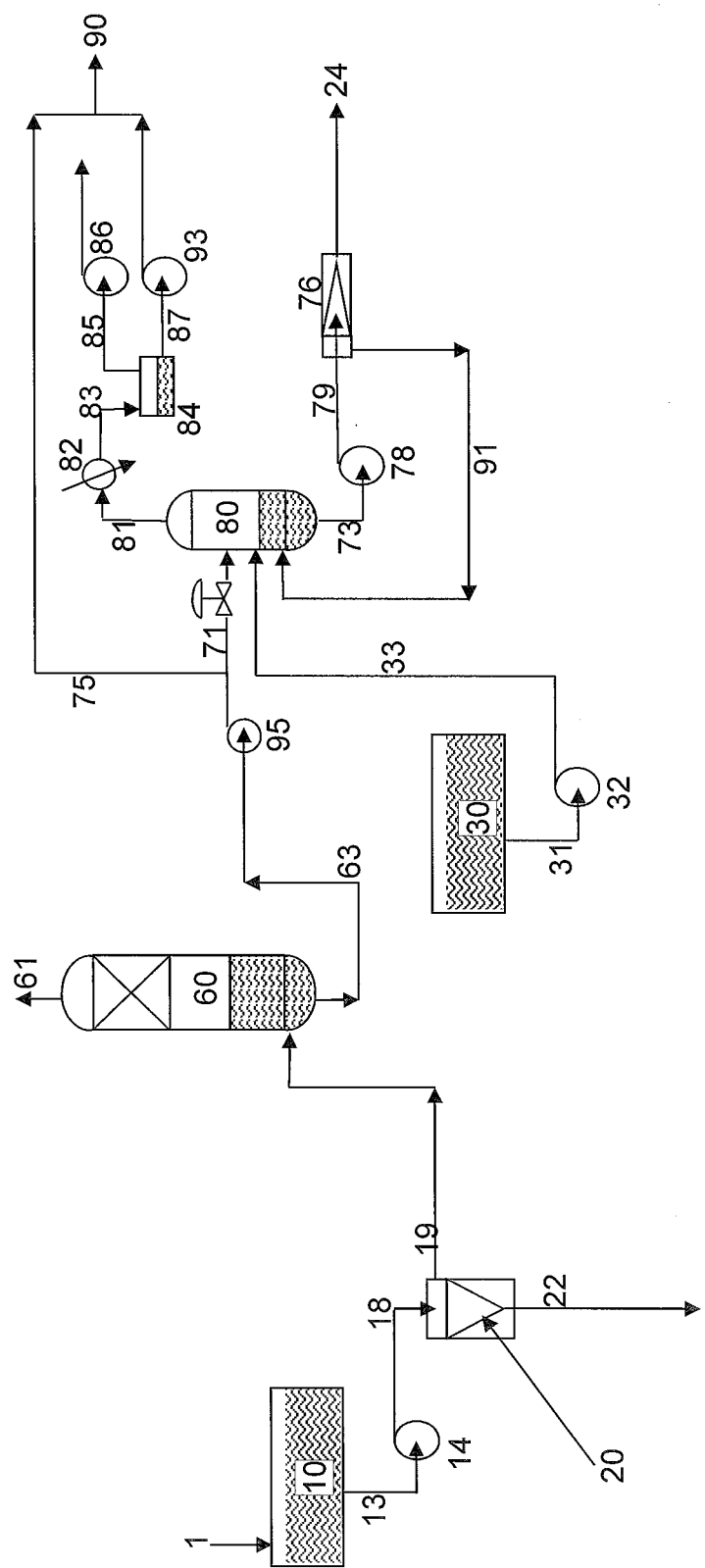
FIG. 1 illustrates an example of a hydrate inhibitor recovery process including a first embodiment of the present invention.

The present invention will now be discussed in further detail with reference to the enclosed figures. The figures are schematic illustrations of embodiments of systems and methods according to the present invention. A person skilled in the art will understand that details such as valves, supply of heating and cooling media etc. are omitted to better illustrate the main principles of the present invention. In the figures equal reference signs are used to refer to equal elements. FIG. 1 shows a full hydrate inhibitor recovery process including one embodiment of the present invention. The figure illustrates one of many possible processes and it will be appreciated that the present invention is equally applicable for use with other such processes.

The embodiment illustrated on FIG. 1 comprises addition of divalent cations in a slip stream reclaimer.

In FIG. 1 the recovery process is illustrated as a three step process, pre-treatment, re-concentration and reclamation. A mixture of water, hydrate inhibitor and salts are obtained by phase separation of the well stream and enters the system as stream 1, also called Rich MEG which is passed to a holding vessel 10 where the alkalinity and pH is controlled and the rich MEG is heated (not shown) and held, or circulated, to obtain forced precipitation of divalent cations as inorganic salts in the rich MEG.

A stream 13 from the holding vessel 10 is passed via pump 14 as stream 18 into a solid separation unit 20. The unit is illustrated as a disk stack type centrifuge but other methods for solid separation are equally applicable. The disc stack type centrifuge can handle the full process flow. Stream 22 comprising the solid salt particles is taken out of the system. The particle free liquid containing dissolved salts is transported as stream 19 to the second recovery process.

The stream 19 enters the main re-concentration unit 60, wherein water is evaporated by heating (not shown) and leaves over the top as stream 61. The liquid stream 63 leaving the main re-concentration unit 60 comprises partly lean concentrated hydrate inhibitor. The pump 95 transports the partly lean hydrate inhibitor. The main part thereof is transported via line 75 to the lean hydrate inhibitor stream 90 applicable for reuse. However to limit and control the salt concentration a slip stream 71 is removed for further processing. The slip stream is fed via a valve to a column 80 and the hydrate inhibitor is evaporated by heating (not shown) under vacuum provided by vacuum pump 86 connected to the top over line 85. The vapour stream 81 is cooled in heat exchanger 82 which results in condensation of the evaporated hydrate inhibitor. Via line 83 the top stream is fed to a vacuum receiver 84. The condensed salt free hydrate inhibitor slip stream is supplied to the lean hydrate inhibitor stream 90 by pump 93 via line 87.

To obtain precipitation of carboxylic acid salts within the column 80 a stream 33 is added containing chloride or other soluble salts of divalent cations that form carboxylic acid salt having low solubility in the hydrate inhibitor. The tank 30 contains a fluid comprising divalent ions such as $BaCl_2$ that form carboxylic acid salt with low solubility in the hydrate inhibitor. The fluid containing dissolved divalent cations is passed via line 31 and pump 32 through line 33 into column 80. Carboxylate ions present in the hydrate inhibitor slip stream precipitate as salts of the divalent cations within the column 80.

A bottom stream 73 is via pump 78 fed as stream 79 to a centrifuge unit 76, preferably a decanter type centrifuge, to obtain a stream 24 comprising salt particles and a liquid stream 91 which is recycled to the column 80. The stream 24 comprising salt particles from the reclamation process includes carboxylic acid salts. The streams 24 and 22 may be treated further to recover additional hydrate inhibitor.

Figure 2:
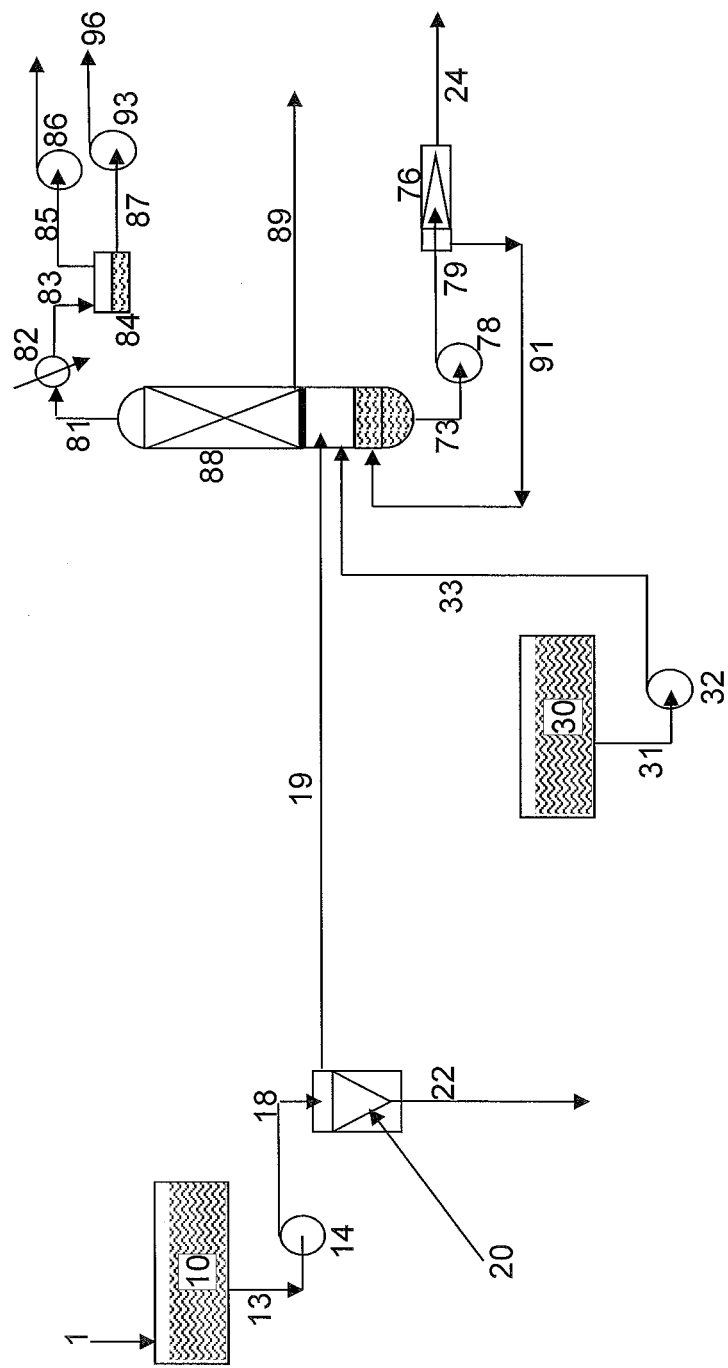
FIG. 2 schematically illustrates another hydrate inhibitor recovery process including a second embodiment of the present invention.

FIG. 2 illustrates another embodiment of the present invention wherein the main unit of the reclamation is a flash separator unit 88 installed in exchange of column 80. This eliminates the need for the separate water removal section in FIG. 1 represented by column 60. In the embodiment of FIG. 2 the stream 19 is fed directly into the flash separation unit 88. The top stream 81 is generally handled in the same way as the top stream from column 80 and the vacuum pump 86 drives both the flash separator and the recirculation of sweep gas. However the liquid stream 96 from the separator 84 will consist of produced water and can be further treated as such. Lean hydrate inhibitor is obtained as stream 89 from a tray within the flash separator arranged above the inlet for stream 19. Here a fluid 33 containing divalent ions that form carboxylic acid salt is added to the full stream reclaimer, the flash separator unit 88. The full stream reclaimer 88 processes the partly rich hydrate inhibitor stream 19. Partly rich as used here refers to the rich hydrate inhibitor obtained after the pre-treatment. In an alternative embodiment (not illustrated) the flash separator unit 88 comprises two separate vessels where produced water and lean HI separation takes place in the second vessel. The fluid 33 is added to the first vessel.

Figure 3:
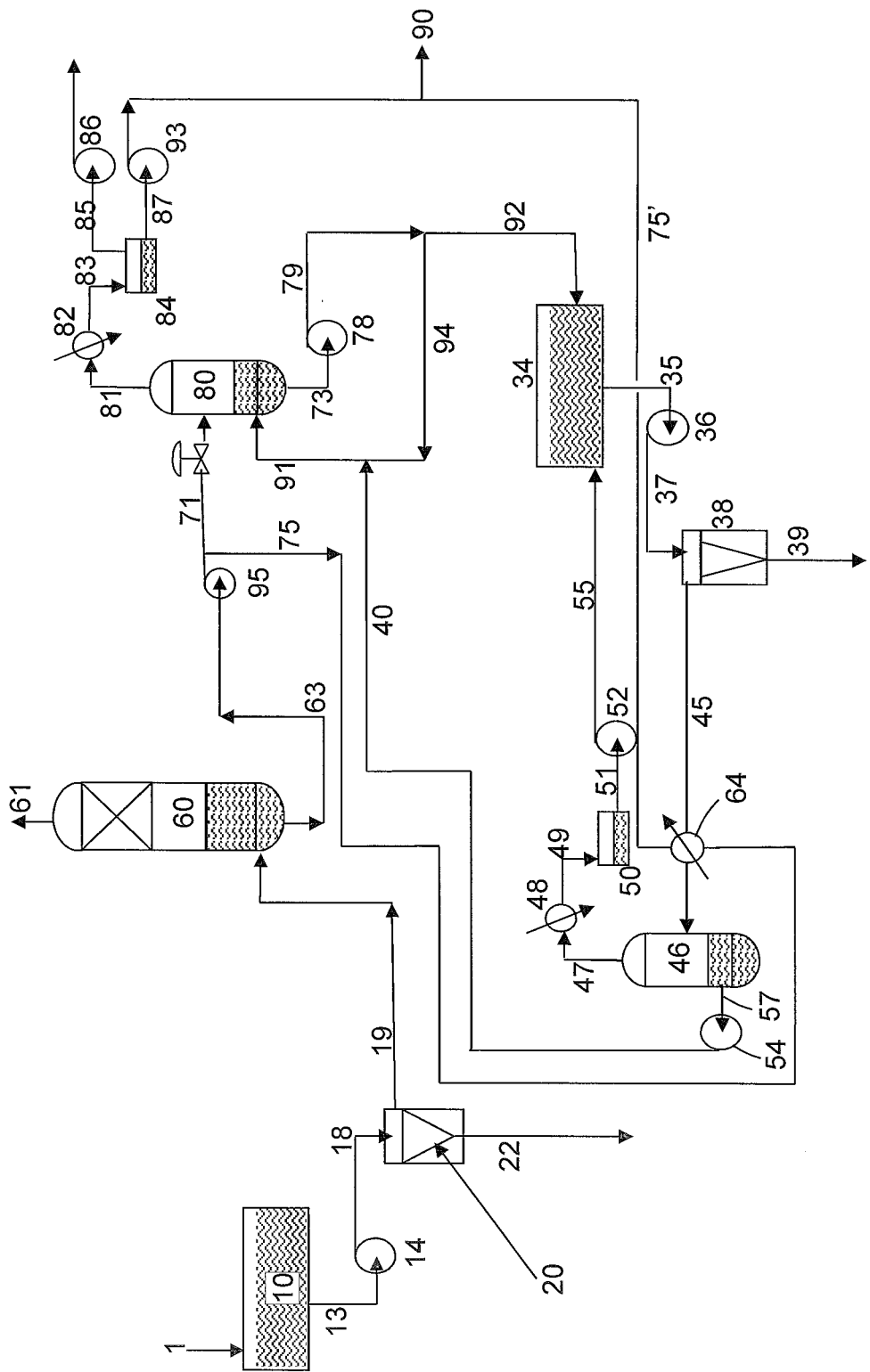
FIG. 3 schematically illustrates yet another hydrate inhibitor recovery process including a third embodiment of the present invention.

FIG. 3 illustrates an alternative embodiment of the present invention. In this embodiment the carboxylic acid salts are removed in a separate system. The main hydrate inhibitor treatment process is performed as shown on FIG. 1. Equal reference numbers are used for equal units. A slip stream 71 is fed to the reclaimer 80 and the main part is transported trough line 75/75' to the lean inhibitor line 90. The only difference in this part of the system compared to FIG. 1 is that heat is removed in a heat exchanger 64 to improve the energy efficiency. Whereas the system according to FIG. 1 relied on the addition of divalent cations to obtain precipitation of carboxylic acid salts, the system according to FIG. 3 utilizes addition of an antisolvent to lower the solubility of the carboxylic acid salts and thereby obtain precipitation. The bottom stream 79 from the reclaimer 80 is passed on as stream 92 into a precipitation tank 34 where it is mixed with an antisolvent stream 55. The stream 92 comprises monovalent inorganic salts as well as the carboxylic acid salts. A part of the stream 79 may via line 94 and 91 be recycled directly back to the reclaimer 80 to keep the bottom fluid in motion and avoid sedimentation of inorganic salts within the system. The need for and the size of the recycle stream 94 depends on the size of stream 92 and the amount of salts to be continually removed to keep the salt content of the reclaimer 80 at an acceptable level.

The introduction of antisolvent to the hydrate inhibitor stream 92 comprising monovalant inorganic salts and carboxlic acid salts reduces the solubility of the carboxylic acid salts and thereby result in precipitation thereof. A bottom stream 35 from the precipitation tank 34 is pumped by pump 36 and line 37 to a solid separation unit 38. The unit is illustrated as a decanter centrifuge but other methods for solid separation are equally applicable such as rotating separation equipment or a gravity separator or a combination thereof. The remaining liquid containing dissolved salts is transported as stream 45 to an antisolvent recovery process. Leaving through line 39 is a mixture of precipitated inorganic monovalent salts and the precipitated carboxylic acid salts.

The remaining particle free liquid 45 is heated in heat exchanger 64 by heat exchange with the main part of the treated hydrate inhibitor stream 75. In an alternative embodiment (not illustrated) additional heat from external sources can be added, depending upon the sizes of stream 75 and 45. The heated remaining liquid stream is fed to a distillation column 46 to separate the antisolvent from the rest of the liquid stream. The antisolvent is evaporated and removed over the top as stream 47 whereas the bottom hydrate inhibitor is returned as stream 40 to the reclaimer 80 via line 57, pump 54 and the recycle loop stream 94. The evaporated antisolvent is passed via line 47 to cooler 48 and further via line 49 to antisolvent tank 50. The antisolvent can be continuously reused and accordingly the line 51 transports the antisolvent via pump 52 and line 55 into the precipitation tank 34. The heat exchanger 48 condenses and cools the antisolvent to control the temperature in the precipitation tank 34, as the solubility of the carboxylic acid salts decreases with decreasing temperatures.

Figure 4:
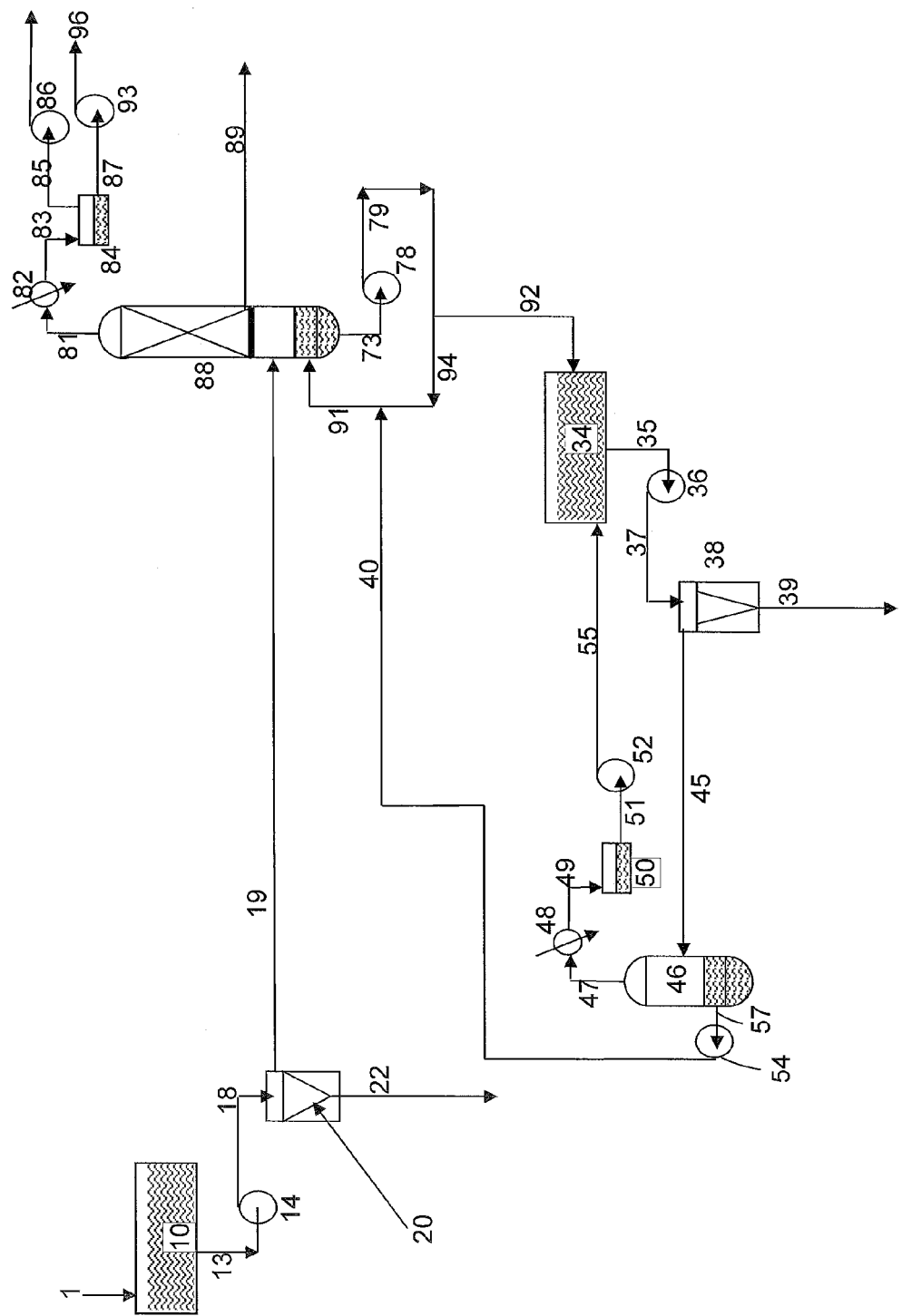
FIG. 4 schematically illustrates yet another hydrate inhibitor recovery process including a fourth embodiment of the present invention.
Figure 10:
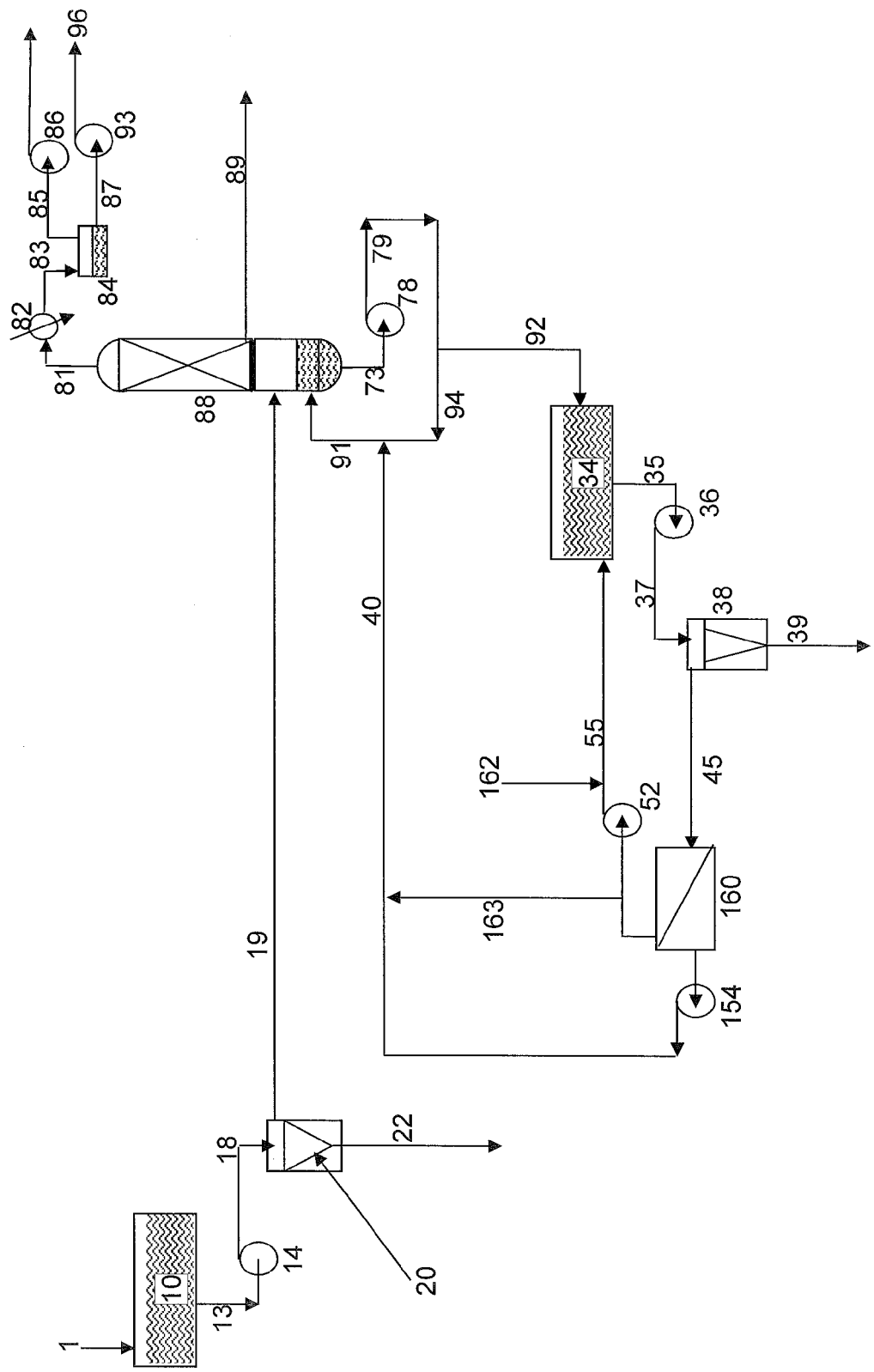
FIG. 10 schematically illustrates yet another hydrate inhibitor recovery process including a seventh embodiment of the present invention.

FIG. 10 illustrates an alternative embodiment of the present invention, wherein the initial method is equivalent to the embodiment illustrated on FIG. 3. In the embodiment on FIG. 10 the antisolvent is separated and or recovered from solids free HI-antisolvent mixture 45 and recycled back to precipitation tank 34 using a membrane separation process 160, and hydrate inhibitor is returned via pump 154 as stream 40 to the reclaimer 88. Here make up of antisolvent from any loss from system, by for example from separator 39, is added in by process line 162. In case the membrane separation process 160 does not separate all anti solvent from the hydrate inhibitor, a portion of the flow can be returned to the reclaimer 88, either continuously via line 163 or batch vise directly (not shown) from precipitation tank 34. FIG. 4 illustrates an alternative embodiment of the present invention. Here a full stream reclaimer as disclosed in FIG. 2 is employed, but the precipitation of the carboxylic acid salts is obtained in a separate system outside full stream reclaimer using an antisolvent to lower the solvability of the salts as described in connection with FIG. 3. The monovalent inorganic salts are removed within the same separate system. The use of a full stream reclaimer does not provide a main lean inhibitor stream 75 applicable for heating the liquid stream 45, accordingly the illustrated embodiment does not comprise such heat integration. Heat for the distillation process in column 46 may be provided by other means (not shown). Recovered hydrate inhibitor is returned as stream 40 to the reclaimer 88 via line 57, pump 54 and the recycle loop stream 94.

Figure 5:
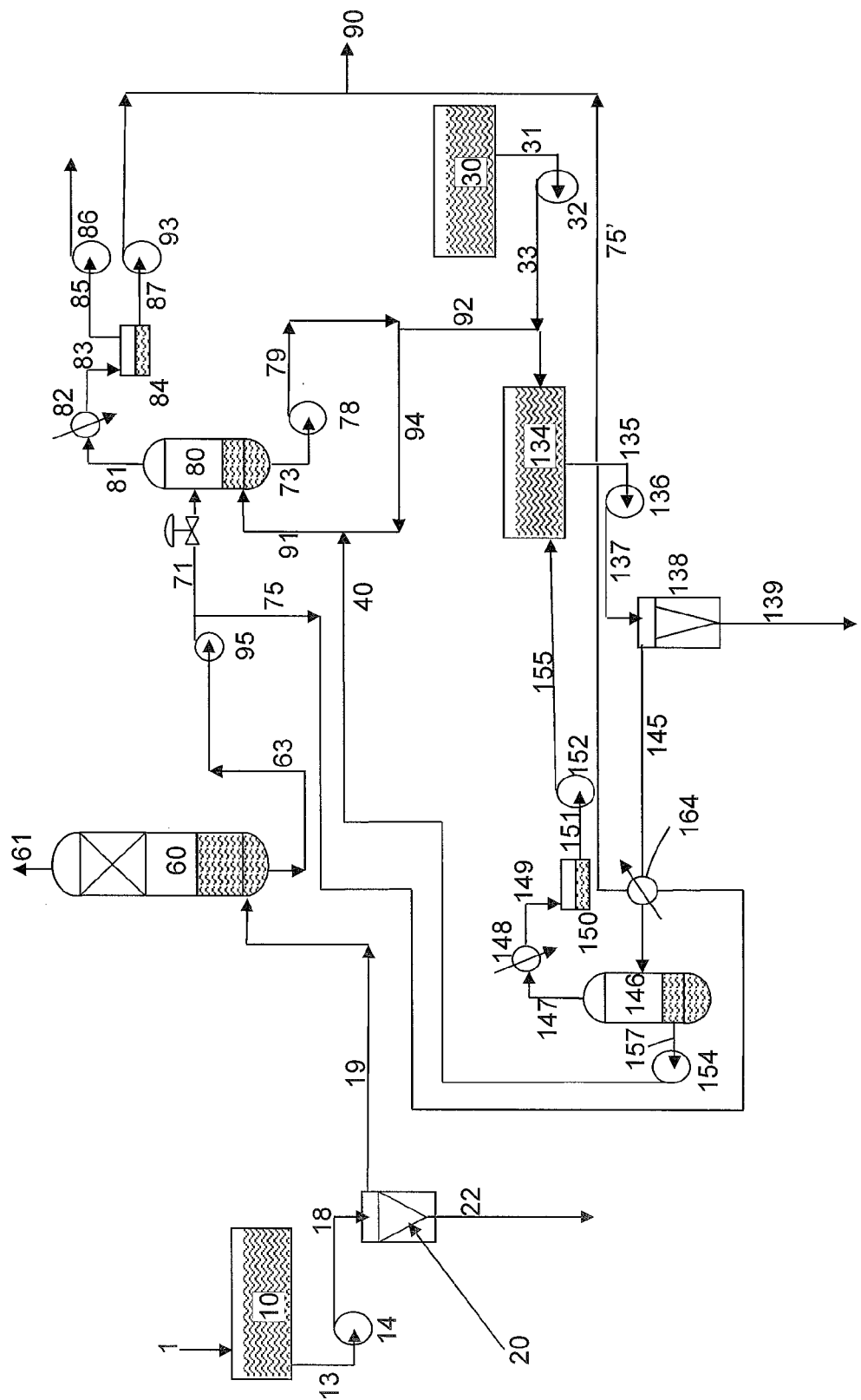
FIG. 5 schematically illustrates yet another hydrate inhibitor recovery process including a fifth embodiment of the present invention.

FIG. 5 illustrates a fifth embodiment of the present invention wherein the precipitation of the carboxylic acid salts is obtained through a combination of addition of divalent cations and antisolvent in a separate system outside of the slip stream reclaimer. This embodiment is a combination of the solutions shown on FIGS. 1 and 3. A slip stream 71 is fed to the reclaimer 80 and a slip stream 92, taken from the bottom recycle stream is passed through a separate system for precipitating carboxylic acid salts and for separating the precipitated salts together with precipitated monovalent salts. From a tank 30 via line 31, pump 32 and line 33 a stream containing dissolved divalent cations are added to the stream 92 prior to or when entering a precipitation tank 134. Via a line 155 an antisolvent stream is added to the precipitation tank, resulting in the precipitation of carboxylic acid salts. The line 135 transports the fluid including the precipitated carboxylic acid salts and the monovalent inorganic salts via pump 136 and line 137 to a separation unit 138. The precipitated carboxylic acid salts and monovalent inorganic salts are separated out in separation unit 138. Leaving through line 39 is a mixture of precipitated inorganic monovalent salts and the precipitated carboxylic acid salts.

The liquid stream from the separation unit 138 is passed on through line 145 to a distillation column 146. The liquid stream is heated in heat exchanger 164 through heat exchange with the main inhibitor stream 75. In an alternative embodiment (not illustrated) additional heat from external sources can be added, depending upon the sizes of stream 75 and 145.

Figure 6:
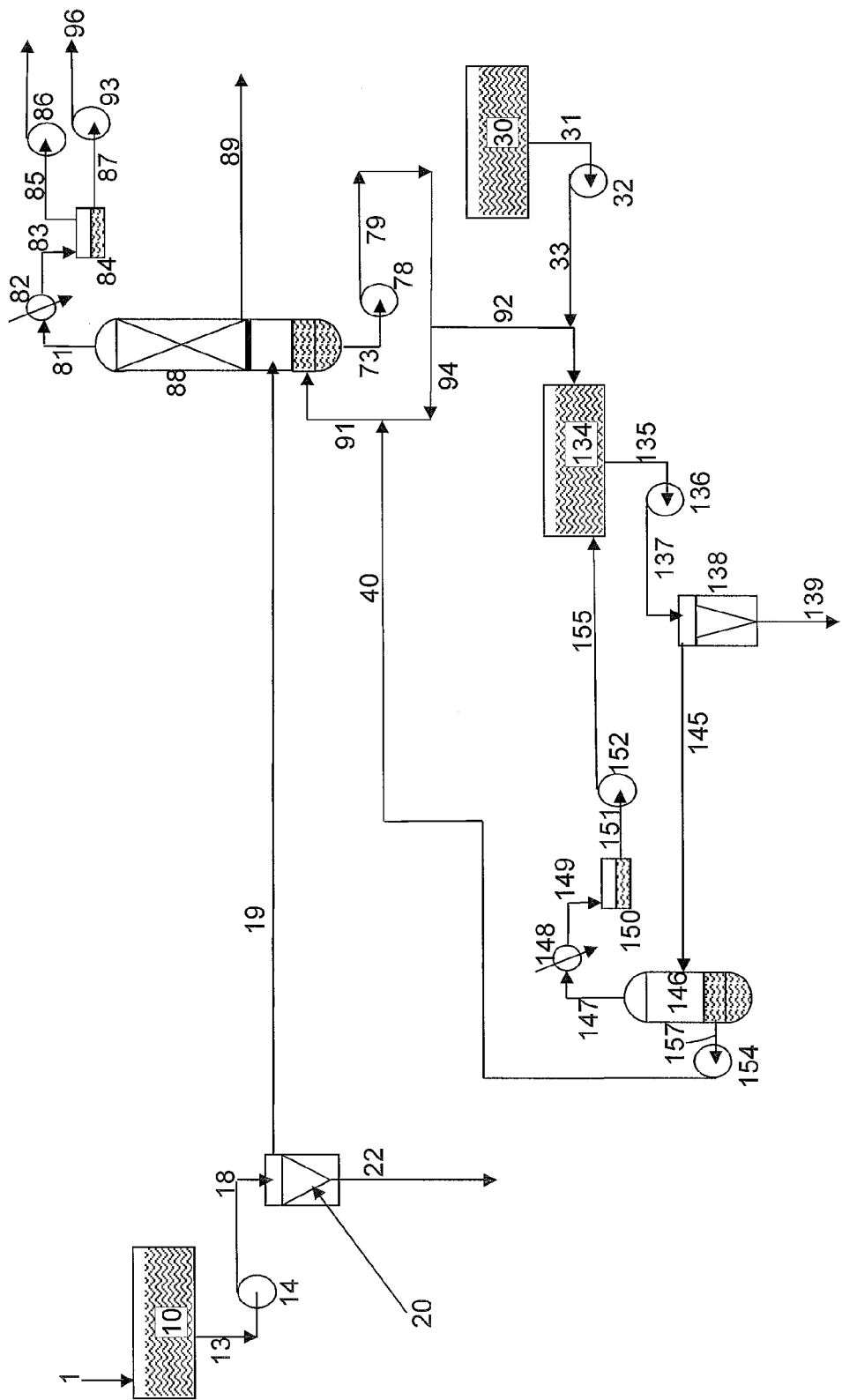
FIG. 6 schematically illustrates yet another hydrate inhibitor recovery process including a sixth embodiment of the present invention.

FIG. 6 illustrates an embodiment of the present invention comprising precipitating divalent salts of the carboxylic acids using a combination of antisolvent and divalent cations in a separate system outside a full stream reclaimer. The embodiment is a combination of the embodiments illustrated on FIGS. 2 and 4, and the principles of the separate system are equal to the separate system of FIG. 5. In the embodiment of FIG. 6 a slip stream 92 is taken from the bottom recycling loop and passed into a precipitation tank 134 together with a stream 33 comprising dissolved divalent cations and antisolvent stream 155. The precipitated carboxylic acid salts and monovalent inorganic salts are separated out in separation unit 138. The recovered liquid stream 145 is passed onto a distillation unit 146 where the antisolvent is distilled of for reuse. Heat is added in the distillation unit 146 to achieve distillation. The line 40 returns the hydrate inhibitor to the reclaimer column 88.

Figure 7:
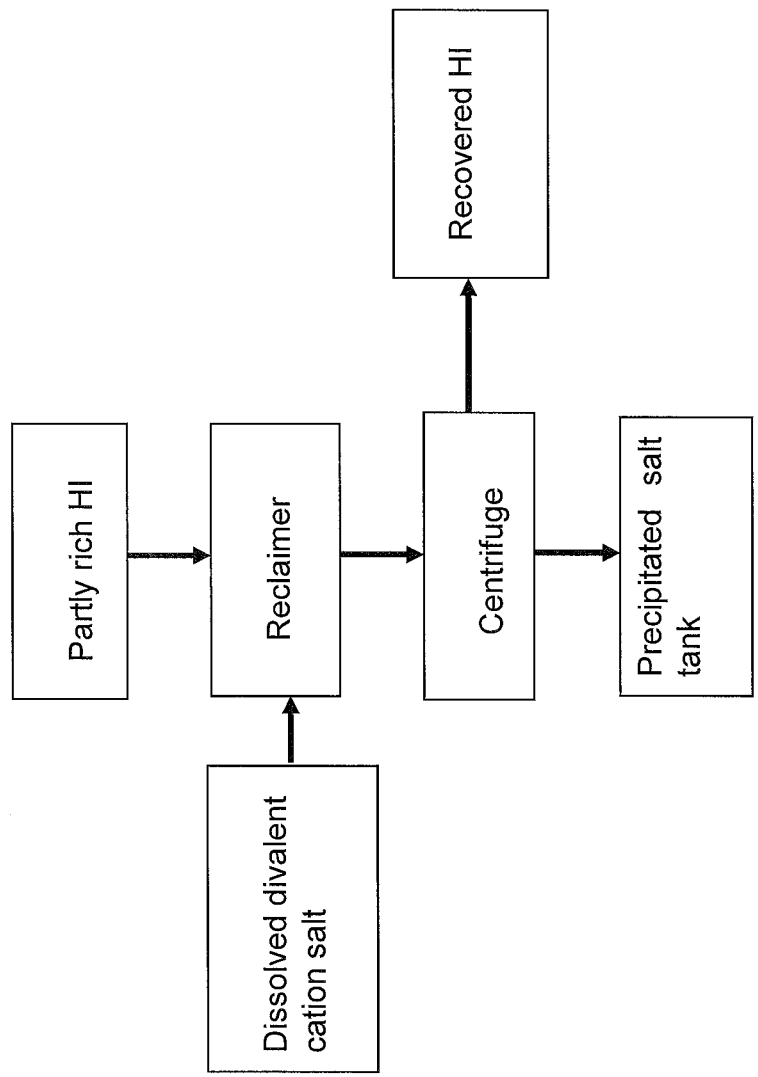
FIG. 7 is a block diagram illustrates an embodiment of the present invention.
Figure 8:
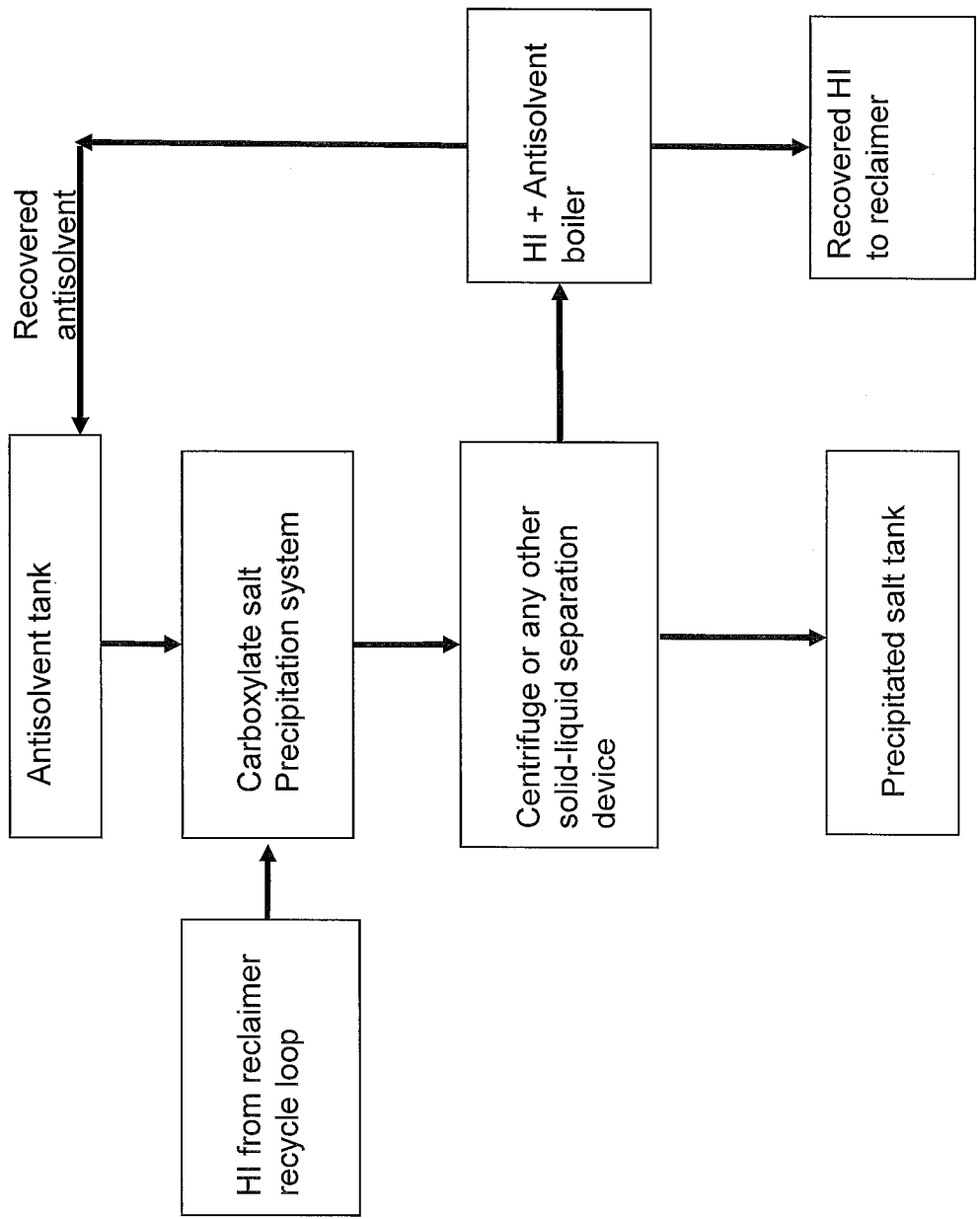
FIG. 8 is a block diagram illustrates another embodiment of the present invention.
Figure 9:
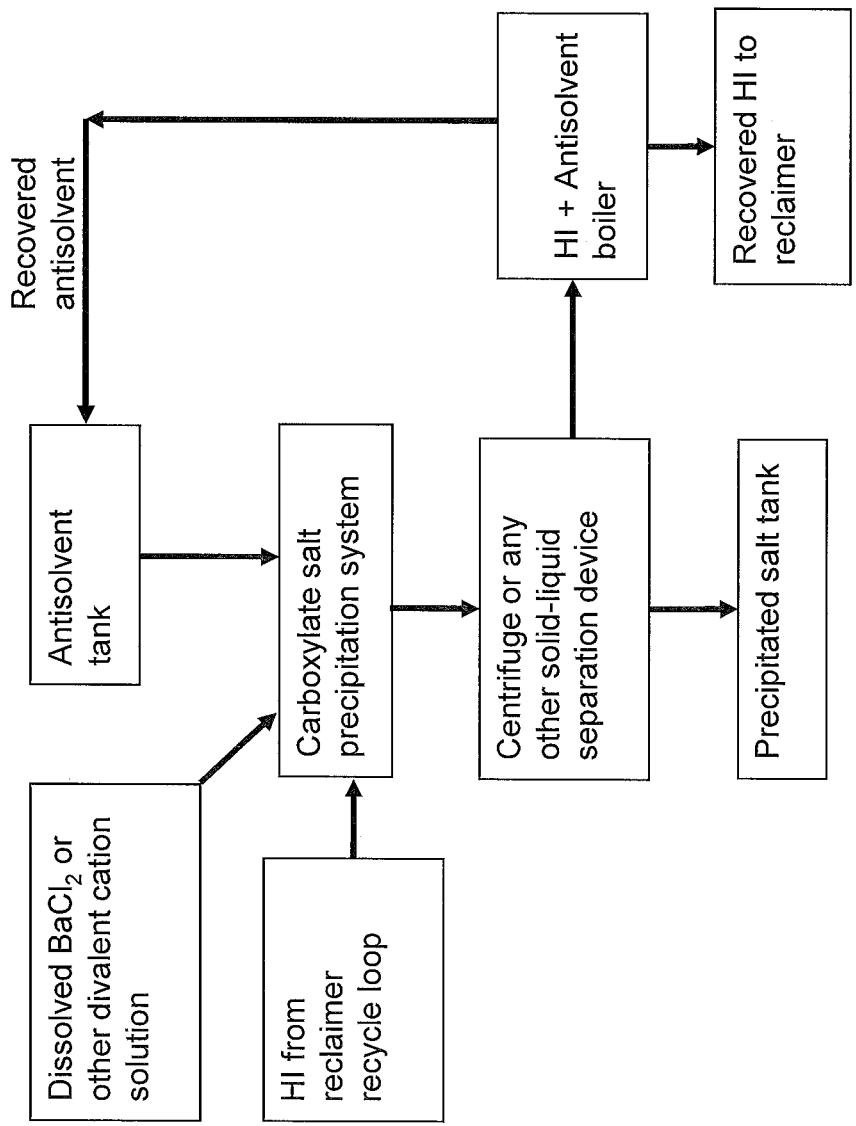
FIG. 9 is a block diagram illustrates yet another embodiment of the present invention.

Whereas the FIGS. 1-6 show detailed embodiments of the present invention the FIGS. 7 to 9 show block diagrams representing the main elements of embodiments of the present invention. Accordingly FIG. 7 illustrates the process where a solution comprising dissolved divalent cations, such as $Ba^{2+}$, $Ca^{2+}$, $Mg^{2+}$, or $Sr^{2+}$, are added to the reclaimer receiving partly rich hydrate inhibitor (HI). In the reclaimer solid particles of carboxylic acid salts are formed along with other salt particles such as NaCl. The salt particles are removed in a centrifuge or another type of solid separation unit providing a recovered hydrate inhibitor stream and a stream of salt particles transferred to a precipitated salt tank.

The system illustrated by the block diagram of FIG. 8 is the various process steps during precipitation of monovalent salts of carboxylic acids using alcohols or ketones as antisolvents. The HI from the reclaimer recycle loop is mixed with antisolvent in the carboxylate salt precipitation system. The precipitated salts are separated from the liquid in a centrifuge or any other solid-liquid separation device resulting in a stream comprising the solid salt particles being transferred to a precipitated salt tank and a liquid stream being transferred to a HI+antisolvent boiler wherein the antisolvent is boiled off and transferred to an antisolvent tank for reuse. The remaining liquid comprises recovered HI which is transferred back to the reclaimer.

FIG. 9 is a block diagram showing various process steps during precipitation of salts of carboxylic acids using alcohols or ketones as antisolvents and adding a source of divalent cations. Depending on the conditions mono and/or divalent carboxylic acids salts will be formed. HI from a reclaimer recycle loop is mixed with antisolvent from an antisolvent tank and a solution containing dissolved divalent cations in a carboxylate salt precipitation system. The solution is prepared using a solvent selected from water, antisolvent, HI, other applicable solvents or combinations thereof. The precipitated salts are separated from the liquid in a centrifuge or any other solid-liquid separation device resulting in a stream comprising the solid salt particles being transferred to a precipitated salt tank and a liquid stream being transferred to a HI+antisolvent boiler, wherein the antisolvent is boiled off and transferred to an antisolvent tank for reuse. The remaining liquid comprises recovered HI which is transferred back to the reclaimer. The solvent used for the divalent cation solution may follow the recovered HI back to the reclaimer or may be boiled off together with the antisolvent, depending on the boiling point of the solvent and the temperature within the boiler.

The invention claimed is:

1. A method for precipitation and separation of carboxylic acid salts from a hydrate inhibitor fluid stream comprising lowering the solubility of the carboxylic acid salts to force precipitation of carboxylic acid salts and separation of the precipitated carboxylic acid salts by separation of the solid precipitated salts from the hydrate inhibitor solution, wherein the hydrate inhibitor comprises at least one glycol based inhibitor, and wherein the lowering of the solubility is performed by adding an antisolvent to the hydrate inhibitor fluid stream.

2. The method according to claim 1, wherein the lowering of the solubility is further performed by adding a solution of an inorganic salt comprising divalent cations.

3. The method according to claim 2, wherein the divalent cations are selected from the group consisting of $Ca^{2+}$, $Ba^{2+}$, $Sr^{2+}$, $Mg^{2+}$, and $Fe^{2+}$.

4. The method according to claim 2 wherein the inorganic salt is $BaCl_2$.

5. The method according to claim 1, wherein the antisolvent is selected from the group consisting of alcohols and ketones.

6. The method according to claim 1, wherein the antisolvent is selected from the group consisting of butanol, iso-propanol, and acetone.

7. The method according to claim 1, wherein the hydrate inhibitor is MEG.

8. The method according to claim 1, wherein the method is performed on a slip stream from a partly lean hydrate inhibitor recycle stream.

9. The method according to claim 1, wherein the method comprises separation of the added antisolvent after the separation of solids, and where heat is transferred from the remaining partly lean hydrate inhibitor recycle stream to aid the separation of the anti solvent.

10. The method according to claim 1, wherein the method comprises separation of the added antisolvent after the separation of solids using a membrane separation process.

11. The method according to claim 1, wherein the method comprises separation of the added antisolvent after the separation of solids using a distillation process.

12. The method according to claim 11, wherein the method comprises cooling of the antisolvent and reuse of the antisolvent, and wherein the hydrate inhibitor fluid stream is recycled.

13. The method according to claim 1, wherein the temperature during the precipitation is 0 to 130° C.

14. The method according to claim 1, wherein the antisolvent is selected from the group consisting of methanol, ethanol, butanol, iso-propanol, and acetone.

* * * * *